(12) United States Patent
Liu et al.

(10) Patent No.: US 8,476,469 B2
(45) Date of Patent: Jul. 2, 2013

(54) PROCESS FOR PRODUCING C1-C4 ALKYL NITRITE

(75) Inventors: Juntao Liu, Shanghai (CN); Weimin Yang, Shanghai (CN); Wanmin Wang, Shanghai (CN); Linna Zhang, Shanghai (CN)

(73) Assignees: China Petroleum & Chemical Corporation, Beijing (CN); Shanghai Research Institute of Petrochemical Technology SINOPEC, Shanghai (CN)

( * ) Notice: Subject to any disclaimer, the term of this patent is extended or adjusted under 35 U.S.C. 154(b) by 291 days.

(21) Appl. No.: 13/087,285

(22) Filed: Apr. 14, 2011

(65) Prior Publication Data

US 2011/0257424 A1    Oct. 20, 2011

(30) Foreign Application Priority Data

Apr. 15, 2010    (CN) .......................... 2010 1 0147049

(51) Int. Cl.
*C07C 203/00*    (2006.01)
(52) U.S. Cl.
USPC .......................................................... 558/488
(58) Field of Classification Search
USPC .......................................................... 558/488
See application file for complete search history.

(56) References Cited

U.S. PATENT DOCUMENTS

| 4,353,843 A | * | 10/1982 | Doumaux et al. ............ 558/488 |
| 4,879,401 A | | 11/1989 | Doumaux, Jr. et al. |
| 5,649,322 A | | 7/1997 | Landscheidt et al. |
| 2005/0038282 A1 | | 2/2005 | Sugise et al. |

FOREIGN PATENT DOCUMENTS

| CN | 1148589 A | 4/1997 |
| CN | 101143821 A | 3/2008 |
| EP | 0 310 191 A2 | 9/1987 |

* cited by examiner

*Primary Examiner* — Joseph Kosack
*Assistant Examiner* — Matthew Coughlin
(74) *Attorney, Agent, or Firm* — Enshan Hong; VLP Law Group LLP

(57) ABSTRACT

A process of producing $C_1$-$C_4$ alkyl nitrite, comprising the following steps: a) firstly feeding nitrogen oxide and oxygen into Reactor I, contacting with an aluminosilicate catalyst, and reacting to produce an effluent I containing $NO_2$ and unreacted NO; b) feeding the effluent I and $C_1$-$C_4$ alkanol into Reactor II, and reacting to produce an effluent II containing $C_1$-$C_4$ alkyl nitrite; and c) separating the effluent II containing $C_1$-$C_4$ alkyl nitrite to obtain $C_1$-$C_4$ alkyl nitrite; wherein reactor I is a fixed bed reactor, and Reactor II is a rotating high-gravity reactor; said nitrogen oxide in step a) is NO, or a mixed gas containing NO and one or more of $N_2O_3$ and $NO_2$, wherein the molar number of NO is greater than that of $NO_2$, if any; and the molar ratio of NO in nitrogen oxide to oxygen is 4-25:1.

15 Claims, No Drawings

PROCESS FOR PRODUCING C1-C4 ALKYL NITRITE

BACKGROUND OF THE INVENTION

1. Field of the Invention

The present invention relates to a process for producing $C_1$-$C_4$ alkyl nitrite, in particular a process for producing $C_1$-$C_4$ alkyl nitrite by reaction in a rotating high-gravity reactor, wherein $C_1$-$C_4$ alkyl nitrite is useful in the production of oxalate by CO coupling.

2. Description of the Related Art

Oxalate is an important organic chemical material, and widely used in fine chemicals for the production of various dyes, medicines, important solvents, extractants and intermediates. In $21^{st}$ century, oxalate as a degradable environmental-protection-type engineering plastic monomer is internationally and widely recognized. In addition, hydrolysis of oxalate at normal pressure can produce oxalic acid, and aminolysis of oxalate at normal pressure can produce high grade sustained-release fertilizer—oxamide. Oxalate can also be used as solvent for production of medicines, dye intermediates and the like. For example, various condensation reactions can be carried out by using oxalate together with fatty acid esters, cyclohexylacetophenone, amino alcohols and many heterocyclic compounds. Oxalate can also be used for synthesizing thymine as hormone in the medicine. Low pressure hydrogenation of oxalate can be used for producing ethylene glycol which is a very important chemical raw material. Currently, ethylene glycol is heavily dependent on production via the petroleum routine and has a higher cost. China imports a lot of ethylene glycol each year, and the import volume in 2007 was close to 4,800,000 tons.

The conventional process for production of oxalate involves preparing by esterification of oxalic acid with alcohols, which has a high production process cost, high energy consumption, heavy pollution and unreasonable utilization of raw materials. People are seeking for a low cost and environment-friendly process route. In the 1960s, D. F. Fenton of Integrated Oil Company, U.S.A. found that dialkyl oxalate could be directly synthesized from CO, alcohols and oxygen by oxidization-carbonylation. From then on, UBE Industries Ltd., Japan and ARCO, U.S.A. successively carried on studies and developments in such field.

As seen from the development course, the synthesis of oxalate by the CO oxidization-coupling method can be divided into the liquid phase method and the gaseous phase method. The synthesis of oxalate by the CO liquid phase method requires more stringent conditions: the reaction is conducted at high pressure; the apparatus is easily corroded by the liquid phase system; and the catalyst is easy to lose during the reaction. The gaseous phase method for producing oxalate by CO coupling is advantageous. Sequentially, UBE Industries Ltd., Japan and Montedison S.P.A, Italy have also developed studies on the gaseous phase method in 1978, wherein the process for synthesizing oxalate by gaseous catalysis developed by UBE Industries Ltd. is conducted at a pressure of 0.5 MPa and a temperature of 80-150° C.

The reaction procedures for synthesizing oxalate are as follows.

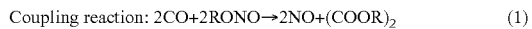

Coupling reaction: $2CO+2RONO \rightarrow 2NO+(COOR)_2$ (1)

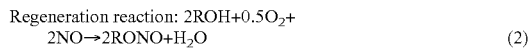

Regeneration reaction: $2ROH+0.5O_2+ 2NO \rightarrow 2RONO+H_2O$ (2)

According to the procedures above, it can be seen that the technical key of such system lies in reasonably utilizing NO, RONO, ROH in said two-step reaction procedures in high selectivity and high efficiency.

However, the truth is that, except for the primary product-alkyl nitrites, side reactions, in particular production of side product-nitric acid, often occur in the reaction procedure of step (2), which necessarily consumes more NO gas, increases energy consumption and cost and erodes the apparatus at the same time. Although there are many documents regarding how to produce alkyl nitrites, there is less report on how to effectively increase selectivity of alkyl nitrites, and to prevent in a better way the side reaction of nitric acid from occurrence.

CN200710060003.4 discloses a process for preparing diethyl oxalate by CO coupling, comprising using the gaseous phase method, coupling CO by catalyzing with a bi-metal supported-type catalyst in the presence of ethyl nitrite to produce a crude product of diethyl oxalate. The reaction is a self-sealing circulation process. CO gas is mixed with ethyl nitrite from the regeneration reactor, preheated and fed into a coupling reactor. After reaction, the gas is condensed and separated to obtain a colorless, transparent condensate of diethyl oxalate. Uncondensed gas containing NO is re-fed into the regeneration reactor to react with ethanol and oxygen and to produce ethyl nitrite, and the resultant ethyl nitrite is recycled to the coupling reactor for continuous use. The selectivity of ethyl nitrite is not mentioned in the invention.

CN 95116136.9 discloses a catalyst for synthesizing oxalate, wherein Zr is used as an auxiliary agent for developing a novel Pd—$Zr/Al_2O_3$ catalyst by the immersion method. Such catalyst is used for synthesizing oxalate from CO and nitrite via gaseous phase catalysis in a fixed bed reaction apparatus. Likewise, such patent document does not involve the selectivity of nitrites and the inhibition against the side reaction of nitric acid.

Hypergravity technology is the new technology strengthening the multiphase flow transmission and reaction process, and widely recognized at home and abroad since it came out in the last century. It has a widely commercial application prospect in the industrial fields of environmental protection and material biological chemistry. However, hypergravity technology is at an application-developing stage at present. Moreover, no study on the application of the rotating high-gravity reactor in the production of $C_1$-$C_4$ alkyl nitrite has been reported.

SUMMARY OF THE INVENTION

The technical problem to be solved by the present invention is the low selectivity of $C_1$-$C_4$ alkyl nitrite in the prior documents, and to provide a novel process for producing $C_1$-$C_4$ alkyl nitrite, wherein such process has the advantage of high selectivity of $C_1$-$C_4$ alkyl nitrite.

In order to solve the technical problem above, the technical solution used in the present invention is as follows: a process for produce $C_1$-$C_4$ alkyl nitrite, comprising the following steps:

a) firstly feeding nitrogen oxide and oxygen into Reactor I, contacting with an aluminosilicate catalyst, and reacting to produce an effluent I containing $NO_2$ and unreacted NO;

b) feeding the effluent I and $C_1$-$C_4$ alkanol into Reactor II, and reacting to produce an effluent II containing $C_1$-$C_4$ alkyl nitrite; and c) separating the effluent II containing $C_1$-$C_4$ alkyl nitrite to obtain $C_1$-$C_4$ alkyl nitrite, wherein Reactor I is a fixed bed reactor, and Reactor II is a rotating high-gravity reactor; said nitrogen oxide in step a) is NO, or a mixed gas containing NO and one or more of $N_2O_3$ and $NO_2$, wherein the molar number of NO is greater than that of $NO_2$, if any; and the molar ratio of NO in nitrogen oxide to oxygen is 4-25:1.

Other objects and features of the present invention will become apparent from the following detailed description.

DETAILED DESCRIPTION OF THE PRESENTLY PREFERRED EMBODIMENTS

In the aforesaid technical solution, the aluminosilicate catalyst is preferably at least one selected from the group consisting of ZSM-5, β-molecular sieves, Y-molecular sieves and MCM-22, more preferably ZSM-5. The aluminosilicate catalyst has a Si/Al molar ratio of 10-800:1, preferably 20-500:1.

The reaction conditions in Reactor I of the technical solution above preferably include a reaction temperature of from 40 to 180° C., a reaction pressure of from −0.05 to 1.0 MPa, and a reaction contacting time of from 0.05 to 100 seconds, wherein the molar ratio of NO in nitrogen oxide to oxygen is 4-20:1. The more preferred reaction conditions in Reactor I include a reaction temperature of preferably from 80 to 170° C., more preferably from 121 to 170° C., more preferably from 125 to 160° C., most preferably from 150 to 158° C., a reaction pressure of from 0.01 to 0.8 MPa, a reaction contacting time of from 2 to 50 seconds, wherein the molar ratio of NO in nitrogen oxide to oxygen is more preferably 4-15:1.

In the aforesaid technical solution, the reaction conditions in Reactor II of the technical solution above preferably include a reaction temperature of from 10 to 100° C. and a reaction pressure of from −0.05 to 1.0 MPa, wherein the molar ratio of $C_1$-$C_4$ alkanol to NO, in the effluent I is 1-15:1. The more preferred reaction conditions in Reactor II include a reaction temperature of from 20 to 70° C. and a reaction pressure of from 0.01 to 0.8 MPa, wherein the molar ratio of $C_1$-$C_4$ alkanol to NO in the effluent I is 1-10:1. $C_1$-$C_4$ alkanol is preferably selected from the group consisting of methanol, ethanol and n-propanol, more preferably methanol. The rotor in the rotating high-gravity reactor preferably has a rotating speed of from 100 to 5,000 rpm, more preferably from 300 to 3,000 rpm.

In one preferred embodiment, a porous filler layer is fixed onto the rotor of the rotating high-gravity reactor, wherein said porous filler layer preferably comprises an inert filler web, a porous web, a stent or a porous plate.

In one preferred embodiment, a resin catalyst layer is fixed onto the rotor of the rotating high-gravity reactor, wherein said resin catalyst is preferably an acidic ion exchange resin catalyst.

In one preferred embodiment, the molar ratio of NO:$NO_2$ in the effluent I is greater than 1.

It is well known that all the substances on earth are attracted by the earth due to the force of gravity. High gravity field is an environment having a strength much greater than that of the gravity field of the earth. The force suffered by the substances in the high gravity field is called high gravity, and the practical technology produced by utilizing the scientific principle of high gravity is called high gravity technology.

High gravity technology is the new technology strengthening the multiphase flow transmission and reaction process, and has a widely commercial application prospect in the industrial fields of environmental protection and material biological chemistry since it came out in the last century. However, high gravity technology is at an application-developing stage at present, which is embodied in the high gravity gas-solid fluidized technology and high gravity gas-liquid mass transfer technology.

In the high gravity environment which is hundreds of to thousands of times the gravity field of the earth, great shearing force tears liquid into liquid membrane, liquid filament and liquid drop in a micrometer or nanometer scale and produces giant and quickly updated phase interfaces, which extremely increases the gas-liquid-contact specific surface area, enhances the interphase mass transfer rate by 1-3 orders of magnitude than that in the conventional column apparatus and extremely strengthens the microscopic mixing and mass transfer processes. The production efficiency per unit device volume is thus increased by 1 to 2 orders of magnitude.

As an apparatus for producing high gravity field, the rotating high-gravity reactor usually consists of gas and liquid inlet pipes, rotor, and gas and liquid outlets. The operating principle thereof is that the gas phase is tangentially introduced into the outer cavity of the rotor via the gas inlet pipe, and fed into the filler from the outer edge of the rotor under the gas action. Liquid is fed into the inner cavity of the rotor via the liquid inlet pipe, and sprayed onto the inner edge of the rotor via sprayer. Under the action of the filler in the rotor, liquid fed into the rotor has an increasing circumferential speed and is pushed to the outer edge of the rotor by the resultant centrifugal force. During such process, liquid is dispersed by the filler and breaks into pieces to form the extremely great and continuously updated surface area, wherein the tortuous flow passages exacerbate the updating of the liquid surfaces. In this way, extremely better mass transfer and reaction conditions are formed inside the rotor. Liquid is thrown to the shell by the rotor, collected and removed from the high gravity machine via the liquid outlet pipe. Gas leaves the rotor from the center of the rotor, and is drawn out via the gas outlet pipe, so as to finish the mass transfer and reaction processes.

Studies show that, during the oxidation-alkylation of nitrogen oxide with oxygen and alcohols to form alkyl nitrites, the reactions conditions, including reaction temperature, reaction pressure, residence time, manner for mixing nitrogen oxide, oxygen and alcohols and the like, all have significant effects on the selectivity of nitrites. In particular, the occurrence of the side reaction of nitric acid formation is closely related to the reaction of the formation of $N_2O_4$ from nitrogen oxide in the raw materials, and thus the technical key is to prevent or minimize the formation of $N_2O_4$.

It is surprisingly found that the $N_2O_4$ content in the product from the reaction between nitrogen oxide and oxygen at a low temperature, in particular less than 50° C., may be as high as more than 10%, but it may be less than 0.5% at a temperature of higher than 100° C. In most cases, the optimal temperature for the alkylation reaction of nitrogen oxide with alcohols ranges from 30 to 60° C. Thus, if oxygen, nitrogen oxide (primarily NO) and alcohols react at a temperature of 30-60° C., there is a high reaction probability of producing $N_2O_4$, so as to have a high probability of the occurrence of nitric acid side reaction and a reduced selectivity of nitrites. If the reaction temperature is increased, the components such as oxygen and alcohols will be further oxidized so as to result in occurrence of side reactions such as aldehyde formation and the like, which also reduces the selectivity of alkyl nitrites.

On the basis of the analyses above, the present invention discloses conducting the catalytic reaction of oxygen and nitrogen oxide at a high temperature to preferably and firstly produce the nitrogen oxide mixture having a NO/$NO_2$ molar ratio of greater than 1 and an extremely low $N_2O_4$ content (e.g. less than 2%, preferably less than 1%), then directly feeding such mixture and alcohols into the alkylation reactor (Reactor II). Studies also find that the oxidization-alkylation reaction of nitrogen oxide with oxygen and alcohols to produce alkyl nitrites is a quick reaction, while the side reaction of nitric acid formation and the like is slower. The reaction rate of the NO oxidization-alkylation reaction is primarily affected by the gas-liquid mass transfer resistance. If the gas-liquid mass transfer efficiency is effectively improved, the probability of producing $N_2O_4$ can be further and effectively reduced, so as to further prevent the side reactions such as nitric acid formation and the like from occurrence.

On the basis of sufficient studies on the features of the oxidization-alkylation reaction of nitrogen oxide with oxygen and alcohols, the technical solution of the present invention further puts forward using a rotating high-gravity reactor as the oxidization-alkylation reactor, sufficiently utilizing the significant advantages that the rotating high-gravity reactor can greatly increase the gas-liquid mass transfer rate by a geometric order of magnitude, thus more effectively promoting the primary reaction and in depth inhibiting the occurrence of side reactions, so as to increase the coefficient of utilization of the raw materials such as NO and the like and to greatly increase the selectivity of nitrites.

In a preferable embodiment of the present invention, nitrogen oxide and oxygen are firstly fed in to Reactor I and in contact with an aluminosilicate catalyst to react and produce the effluent I containing $NO_2$ and unreacted NO, the effluent I and $C_1$-$C_4$ alkanol are fed into Reactor II, and react to produce the effluent II containing $C_1$-$C_4$ alkyl nitrite, then the effluent II containing $C_1$-$C_4$ alkyl nitrite is separated to obtain $C_1$-$C_4$ alkyl nitrite, reactor I is a fixed bed reactor, reactor II is a rotating high-gravity reactor, a porous filler layer is fixed onto the rotor of the rotating high-gravity reactor, said nitrogen oxide is NO or a mixed gas containing NO and one or more from $N_2O_3$ and $NO_2$, wherein the molar number of NO is greater than that of $NO_2$, if any, the molar ratio of NO in nitrogen oxide to oxygen is from 4-15:1, reactor I has a reaction temperature of from 121-170° C., a reaction pressure of from 0.01-0.8 MPa, a reaction contacting time of 2-50 seconds, reactor II has a reaction temperature of 20-70° C., a reaction pressure of 0.01-0.8 MPa, the rotating speed of the rotor of the rotating high-gravity reactor ranges from 300 to 3000 rpm, the molar ratio of $C_1$-$C_4$ alkanol to NO in the effluent I is 1-10:1, and the resulting selectivity of $C_1$-$C_4$ alkyl nitrite may be greater than 99%.

Unless otherwise defined, all technical and scientific terms used herein have the same meaning as commonly understood by one of ordinary skill in the art to which the present invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Throughout this disclosure, various aspects of the present invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 (1-6) should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Except in the operating (working) and comparative examples, or where otherwise explicitly indicated, all numbers in this Description indicating amounts of material or conditions of reaction, physical properties of materials and/or use are to be understood as modified by the word "about". Whenever a numerical range is indicated herein, it is meant to include any cited numeral (fractional or integral) within the indicated range. The phrases "between" a first indicate number and a second indicate number and "ranging/ranges from" a first indicate number "to" a second indicate number are used herein interchangeably and are meant to include the first and second indicated numbers and all the fractional and integral numerals therebetween.

As used herein, the singular form "a", "an", and "the" include plural references unless the context clearly dictates otherwise.

The present invention is further elaborated, but not limited, by the following examples.

EXAMPLES

Example 1

Nitrogen oxide and oxygen were firstly fed in to Reactor I (having the model of FBR10-100 and manufactured by Shanghai Research Institute of Petrochemical Technology, ibid.) and in contact with ZSM-5 molecular sieve catalyst having a Si/Al molar ratio of 400:1, and reacted to produce the effluent I containing $NO_2$ and unreacted NO. The effluent I and methanol were fed into Reactor II, and reacted to produce the effluent II containing methyl nitrite. Then the effluent II containing methyl nitrite was separated to obtain methyl nitrite. Reactor II was a rotating high-gravity reactor, which was the same as the rotating high-gravity reactor in Example 1 of the patent publication CN1895766A (wherein there are a fixed stent and a porous web on the rotor, ibid.). Nitrogen oxide was NO, wherein the molar ratio of NO to oxygen is 6:1. Reactor I had a reaction temperature of 80° C., a reaction pressure of 0.01 MPa, and a reaction contacting time of 2 seconds; Reactor II had a reaction temperature of 30° C., a reaction pressure of 0.01 MPa, and a molar ratio of methanol/NO in the effluent I of 3:1. The rotor speed in the rotating high gravity Reactor II was 1000 rpm. The results showed that the selectivity of methyl nitrite was 99.53%.

Example 2

Nitrogen oxide and oxygen were firstly fed in to Reactor I and in contact with ZSM-5 molecular sieve catalyst having a Si/Al molar ratio of 200:1, and reacted to produce the effluent I containing $NO_2$ and unreacted NO. The effluent I and methanol were fed into Reactor II, and reacted to produce the effluent II containing methyl nitrite. Then the effluent II containing methyl nitrite was separated to obtain methyl nitrite. Reactor II was a rotating high-gravity reactor. Nitrogen oxide was NO, wherein the molar ratio of NO to oxygen is 4:1. Reactor I had a reaction temperature of 121° C., a reaction pressure of −0.05 MPa, and a reaction contacting time of 60 seconds; Reactor II had a reaction temperature of 80° C., a reaction pressure of −0.05 MPa, and a molar ratio of methanol/NO in the effluent I of 9:1. The rotor speed in the rotating high-gravity Reactor II was 800 rpm. The results showed that the selectivity of methyl nitrite was 99.81%.

Example 3

Nitrogen oxide and oxygen were firstly fed in to Reactor I and in contact with ZSM-5 molecular sieve catalyst having a Si/Al molar ratio of 50:1, and reacted to produce the effluent I containing $NO_2$ and unreacted NO. The effluent I and methanol were fed into Reactor II, and reacted to produce the effluent II containing methyl nitrite. Then the effluent II containing methyl nitrite was separated to obtain methyl nitrite. Reactor II was a rotating high-gravity reactor. Nitrogen oxide was NO, wherein the molar ratio of NO to oxygen is 5:1. Reactor I had a reaction temperature of 160° C., a reaction pressure of 0.5 MPa, and a reaction contacting time of 10 seconds; Reactor II had a reaction temperature of 40° C., a reaction pressure of 0.5 MPa, and a molar ratio of methanol/NO in the effluent I of 3.5:1. The rotor speed in the rotating high-gravity Reactor II was 2000 rpm. The results showed that the selectivity of methyl nitrite was 99.38%.

Example 4

Nitrogen oxide and oxygen were firstly fed in to Reactor I and in contact with β-molecular sieve catalyst having a Si/Al molar ratio of 80:1, and reacted to produce the effluent I containing $NO_2$ and unreacted NO. The effluent I and methanol were fed into Reactor II, and reacted to produce the effluent II containing methyl nitrite. Then the effluent II containing methyl nitrite was separated to obtain methyl nitrite. Reactor II was a rotating high-gravity reactor. Nitrogen oxide was the mixture of NO and $NO_2$, wherein the molar ratio of NO to $NO_2$ was 4:1, and the molar ratio of NO to oxygen is 20:1. Reactor I had a reaction temperature of 130° C., a reaction pressure of 0.7 MPa, and a reaction contacting time of 3 seconds; Reactor II had a reaction temperature of 50° C., a reaction pressure of 0.7 MPa, and a molar ratio of methanol/NO in the effluent I of 4:1. The rotor speed in the rotating high-gravity Reactor II was 3000 rpm. The results showed that the selectivity of methyl nitrite was 99.28%.

Example 5

Nitrogen oxide and oxygen were firstly fed in to Reactor I and in contact with β-molecular sieve catalyst having a Si/Al molar ratio of 100:1, and reacted to produce the effluent I containing $NO_2$ and unreacted NO. The effluent I and ethanol were fed into Reactor II, and reacted to produce the effluent II containing ethyl nitrite. Then the effluent II containing ethyl nitrite was separated to obtain ethyl nitrite. Reactor II was a rotating high-gravity reactor. Nitrogen oxide was the mixture of NO and $NO_2$, wherein the molar ratio of NO to $NO_2$ was 6:1, and the molar ratio of NO to oxygen is 15:1. Reactor I had a reaction temperature of 110° C., a reaction pressure of 0.2 MPa, and a reaction contacting time of 1 second; Reactor II had a reaction temperature of 45° C., a reaction pressure of 0.2 MPa, and a molar ratio of ethanol/NO in the effluent I of 5:1. The rotor speed in the rotating high-gravity Reactor II was 4000 rpm. The results showed that the selectivity of ethyl nitrite was 99.65%.

Example 6

Nitrogen oxide and oxygen were firstly fed in to Reactor I and in contact with Y-molecular sieve catalyst having a Si/Al molar ratio of 30:1, and reacted to produce the effluent I containing $NO_2$ and unreacted NO. The effluent I and propanol were fed into Reactor II, and reacted to produce the effluent II containing propyl nitrite. Then the effluent II containing propyl nitrite was separated to obtain propyl nitrite. Reactor II was a rotating high-gravity reactor. Nitrogen oxide was the mixture of NO and $NO_2$, wherein the molar ratio of NO to $NO_2$ was 3:1, and the molar ratio of NO to oxygen is 5:1; Reactor I had a reaction temperature of 130° C., a reaction pressure of 0.3 MPa, and a reaction contacting time of 5 seconds; Reactor II had a reaction temperature of 30° C., a reaction pressure of 0.3 MPa, and a molar ratio of propanol/NO in the effluent I of 15:1. The rotor speed in the rotating high-gravity Reactor II was 4800 rpm. The results showed that the selectivity of propyl nitrite was 99.86%.

Example 7

Nitrogen oxide and oxygen were firstly fed in to Reactor I and in contact with MCM-22 molecular sieve catalyst having a Si/Al molar ratio of 60:1, and reacted to produce the effluent I containing $NO_2$ and unreacted NO. The effluent I and methanol were fed into Reactor II, and reacted to produce the effluent II containing methyl nitrite. Then the effluent II containing methyl nitrite was separated to obtain methyl nitrite. Reactor II was a rotating high-gravity reactor. Nitrogen oxide was the mixture of NO, $NO_2$ and $N_2O_3$, wherein the molar ratio of NO to $NO_2$ to $N_2O_3$ was 4:1:3, and the molar ratio of NO to oxygen is 10:1. Reactor I had a reaction temperature of 125° C., a reaction pressure of 0.1 MPa, and a reaction contacting time of 1.8 seconds; Reactor II had a reaction temperature of 40° C., a reaction pressure of 0.3 MPa, and a molar ratio of methanol/NO in the effluent I of 12:1. The rotor speed in the rotating high-gravity Reactor II was 1500 rpm. The results showed that the selectivity of methyl nitrite was 99.59%.

Example 8

Nitrogen oxide and oxygen were firstly fed in to Reactor I and in contact with MCM-22 molecular sieve catalyst having a Si/Al molar ratio of 200:1, and reacted to produce the effluent I containing $NO_2$ and unreacted NO. The effluent I and methanol were fed into Reactor II, and reacted to produce the effluent II containing methyl nitrite. Then the effluent II containing methyl nitrite was separated to obtain methyl nitrite. Reactor II was a rotating high-gravity reactor. Nitrogen oxide was the mixture of NO and $N_2O_3$, wherein the molar ratio of NO to $N_2O_3$ was 2:1, and the molar ratio of NO to oxygen is 15:1. Reactor I had a reaction temperature of 160° C., a reaction pressure of 0.6 MPa, and a reaction contacting time of 0.5 second; Reactor II had a reaction temperature of 38° C., a reaction pressure of 0.3 MPa, and a molar ratio of methanol/NO in the effluent I of 3.5:1. The rotor speed in the rotating high-gravity Reactor II was 2500 rpm. The results showed that the selectivity of methyl nitrite was 99.53%.

Example 9

Nitrogen oxide and oxygen were firstly fed in to Reactor I and in contact with SAPO-34 molecular sieve catalyst having a Si/Al molar ratio of 10:1, and reacted to produce the effluent I containing $NO_2$ and unreacted NO. The effluent I and methanol were fed into Reactor II, and reacted to produce the effluent II containing methyl nitrite. Then the effluent II containing methyl nitrite was separated to obtain methyl nitrite. Reactor II was a rotating high-gravity reactor. Nitrogen oxide was NO, wherein the molar ratio of NO to oxygen was 4.5:1. Reactor I had a reaction temperature of 90° C., a reaction pressure of 0.1 MPa, and a reaction contacting time of 3 seconds; Reactor II had a reaction temperature of 42° C., a reaction pressure of 0.3 MPa, and a molar ratio of methanol/NO in the effluent I of 3:1. The rotor speed in the rotating high-gravity Reactor II was 1800 rpm. The results showed that the selectivity of methyl nitrite was 99.89%.

Example 10

Nitrogen oxide and oxygen were firstly fed in to Reactor I and in contact with ZSM-5 molecular sieve catalyst having a Si/Al molar ratio of 800:1, and reacted to produce the effluent I containing $NO_2$ and unreacted NO. The effluent I and ethanol were fed into Reactor II, and reacted to produce the effluent II containing ethyl nitrite. Then the effluent II containing ethyl nitrite was separated to obtain ethyl nitrite. Reactor II was a rotating high-gravity reactor. Nitrogen oxide was NO, wherein the molar ratio of NO to oxygen was 5:1. Reactor I had a reaction temperature of 150° C., a reaction pressure of −0.05 MPa, and a reaction contacting time of 3 seconds; Reactor II had a reaction temperature of 20° C., a reaction pressure of −0.05 MPa, and a molar ratio of ethanol/NO in the effluent I of 3.5:1. The rotor speed in the rotating high-gravity Reactor II was 3000 rpm. The results showed that the selectivity of ethyl nitrite was 99.55%.

Example 11

Nitrogen oxide and oxygen were firstly fed in to Reactor I and in contact with ZSM-5 molecular sieve catalyst having a Si/Al molar ratio of 600:1, and reacted to produce the effluent I containing $NO_2$ and unreacted NO. The effluent I and ethanol were fed into Reactor II, and reacted to produce the effluent II containing ethyl nitrite. Then the effluent II containing ethyl nitrite was separated to obtain ethyl nitrite. Reactor II was a rotating high-gravity reactor. Nitrogen oxide was NO, wherein the molar ratio of NO to oxygen was 7:1. Reactor I had a reaction temperature of 140° C., a reaction pressure of 0.5 MPa, and a reaction contacting time of 8 seconds; Reactor II had a reaction temperature of 15° C., a reaction pressure of 0.5 MPa, and a molar ratio of ethanol/NO in the effluent I of 8:1. The rotor speed in the rotating high-gravity Reactor II was 600 rpm. The results showed that the selectivity of ethyl nitrite was 99.38%.

Example 12

Nitrogen oxide and oxygen were firstly fed in to Reactor I and in contact with ZSM-5 molecular sieve catalyst having a Si/Al molar ratio of 600:1, and reacted to produce the effluent I containing $NO_2$ and unreacted NO. The effluent I and methanol were fed into Reactor II, and reacted to produce the effluent II containing methyl nitrite. Then the effluent II containing methyl nitrite was separated to obtain methyl nitrite. Reactor II was a rotating high-gravity reactor, wherein a highly acidic cation exchange resin of the D005 series (Dandong Mingzhu Special Resin Co., Ltd.) was fixed onto the rotor. Nitrogen oxide was NO, wherein the molar ratio of NO to oxygen was 6:1. Reactor I had a reaction temperature of 140° C., a reaction pressure of 0.5 MPa, and a reaction contacting time of 8 seconds; Reactor II had a reaction temperature of 20° C., a reaction pressure of 0.3 MPa, and a molar ratio of methanol/NO in the effluent I of 8:1. The rotor speed in the rotating high-gravity Reactor II was 800 rpm. The results showed that the selectivity of methyl nitrite was 99.93%.

Comparative Example 1

The conditions and reaction materials were the same as those in Example 8, except that there was no Reactor I (i.e. all the reactions were carried out in Reactor II). The results showed that the selectivity of methyl nitrite was 98.8%.

Comparative Example 2

The conditions and reaction materials were the same as those in Example 8, except that Reactor II is a fixed bed reactor (having the model of FBR10-100 and manufactured by Shanghai Research Institute of Petrochemical Technology). The results showed that the selectivity of methyl nitrite was 97.5%.

The technological conditions and results thereof in the aforesaid examples are generalized in the following Table 1.

TABLE 1

| Example No. | $NO:O_2$ (molar ratio) in the raw materials | Reactor I | Catalyst in Rector I | Temperature in Reactor I, ° C. | Pressure in Reactor I, MPa | Contacting time in Reactor I, s |
|---|---|---|---|---|---|---|
| Exp. 1 | 6:1 | Fixed bed | ZSM-5 with a Si/Al molar ratio of 400:1 | 80 | 0.01 | 2 |
| Exp. 2 | 4:1 | Fixed bed | ZSM-5 with a Si/Al molar ratio of 200:1 | 121 | −0.05 | 60 |
| Exp. 3 | 5:1 | Fixed bed | ZSM-5 with a Si/Al molar ratio of 50:1 | 160 | 0.5 | 10 |
| Exp. 4 | 20:1 | Fixed bed | β-molecular sieve with a Si/Al molar ratio of 80:1 | 130 | 0.7 | 3 |
| Exp. 5 | 15:1 | Fixed bed | β-molecular sieve with a Si/Al molar ratio of 100:1 | 110 | 0.2 | 1 |
| Exp. 6 | 5:1 | Fixed bed | γ-molecular sieve with a Si/Al molar ratio of 30:1 | 130 | 0.3 | 5 |
| Exp. 7 | 10:1 | Fixed bed | MCM-22 with a Si/Al molar ratio of 60:1 | 125 | 0.1 | 1.8 |
| Exp. 8 | 15:1 | Fixed bed | MCM-22 with a Si/Al molar ratio of 200:1 | 160 | 0.6 | 0.5 |
| Exp. 9 | 4.5:1 | Fixed bed | SAPO-34 with a Si/Al molar ratio of 10:1 | 90 | 0.1 | 3 |
| Exp. 10 | 5:1 | Fixed bed | ZSM-5 with a Si/Al molar ratio of 800:1 | 150 | −0.05 | 3 |
| Exp. 11 | 7:1 | Fixed bed | ZSM-5 with a Si/Al molar ratio of 600:1 | 140 | 0.5 | 8 |

TABLE 1-continued

| Example No. | | | | | | |
|---|---|---|---|---|---|---|
| Exp. 12 | 6:1 | Fixed bed | ZSM-5 with a Si/Al molar ratio of 600:1 | 140 | 0.5 | 8 |
| Com. Exp. 1 | 15:1 | — | — | — | — | — |
| Com. Exp. 2 | 15:1 | Fixed bed | MCM-22 with a Si/Al molar ratio of 200:1 | 160 | 0.6 | 0.5 |

| Example No. | Reactor II | Temperature in Reactor II, °C. | Pressure in Reactor II, MPa | Molar ratio of alcohol:NO in the effluent I | Selectivity of nitrite, % |
|---|---|---|---|---|---|
| Exp. 1 | Rotating high-gravity reactor (having a rotating speed of 1000 rpm) | 30 | 0.01 | 3:1 | 99.53 |
| Exp. 2 | Rotating high-gravity reactor (having a rotating speed of 800 rpm) | 80 | −0.05 | 9:1 | 99.81 |
| Exp. 3 | Rotating high-gravity reactor (having a rotating speed of 2000 rpm) | 40 | 0.5 | 3.5.:1 | 99.38 |
| Exp. 4 | Rotating high-gravity reactor (having a rotating speed of 3000 rpm) | 50 | 0.7 | 4:1 | 99.28 |
| Exp. 5 | Rotating high-gravity reactor (having a rotating speed of 4000 rpm) | 45 | 0.2 | 5:1 | 99.65 |
| Exp. 6 | Rotating high-gravity reactor (having a rotating speed of 4800 rpm) | 30 | 0.3 | 15:1 | 99.86 |
| Exp. 7 | Rotating high-gravity reactor (having a rotating speed of 1500 rpm) | 40 | 0.3 | 12:1 | 99.59 |
| Exp. 8 | Rotating high-gravity reactor (having a rotating speed of 2500 rpm) | 38 | 0.3 | 3.5:1 | 99.53 |
| Exp. 9 | Rotating high-gravity reactor (having a rotating speed of 1800 rpm) | 42 | 0.3 | 3:1 | 99.89 |
| Exp. 10 | Rotating high-gravity reactor (having a rotating speed of 3000 rpm) | 20 | −0.05 | 3.5:1 | 99.55 |
| Exp. 11 | Rotating high-gravity reactor (having a rotating speed of 600 rpm) | 15 | 0.5 | 8:1 | 99.38 |
| Exp. 12 | Rotating high-gravity reactor (having a rotating speed of 800 rpm) + D005 | 20 | 0.3 | 8:1 | 99.93 |
| Com. Exp. 1 | Rotating high-gravity reactor (having a rotating speed of 2500 rpm)) | 38 | 0.3 | 3.5:1 | 98.8 |
| Com. Exp. 2 | Fixed bed | 38 | 0.3 | 3.5:1 | 97.5 |

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

We claim:

1. A process of producing a $C_1$-$C_4$ alkyl nitrite comprising:
   a) firstly feeding nitrogen oxide and oxygen into Reactor I, contacting with an aluminosilicate catalyst, and reacting to produce an effluent I containing $NO_2$ and unreacted NO;
   b) feeding the effluent I and a $C_1$-$C_4$ alkanol into Reactor II, and reacting to produce an effluent II containing the $C_1$-$C_4$ alkyl nitrite; and
   c) separating the effluent II containing the $C_1$-$C_4$ alkyl nitrite to obtain the $C_1$-$C_4$ alkyl nitrite,
   wherein Reactor I is a fixed bed reactor, and Reactor II is a rotating high-gravity reactor; said nitrogen oxide in step a) is NO, or a mixed gas containing NO and one or more of $N_2O_3$ and $NO_2$, wherein the molar number of NO is greater than that of $NO_2$, if any; and the molar ratio of NO in nitrogen oxide to oxygen is 4-25:1.

2. The process according to claim 1, wherein the aluminosilicate catalyst is at least one selected from the group consisting of ZSM-5, β-molecular sieves, Y-molecular sieves, MCM-22, and combinations thereof, and the aluminosilicate catalyst has a Si/Al molar ratio of 10-800:1.

3. The process according to claim 2, wherein the aluminosilicate catalyst is ZSM-5 and has a Si/Al molar ratio of 20-500:1.

4. The process according to claim 1, wherein a porous filler layer is fixed onto the rotor of the rotating high-gravity reactor.

5. The process according to claim 1, wherein a resin catalyst layer is fixed onto the rotor of the rotating high-gravity reactor.

6. The process according to claim 5, wherein the resin catalyst is an acidic ion exchange resin catalyst.

7. The process according to claim 1, wherein Reactor I has a reaction temperature of from 40 to 180° C., a reaction pressure of from −0.05 to 1.0 MPa, a reaction contacting time of from 0.05 to 100 seconds, and the molar ratio of NO in nitrogen oxide to oxygen is 4-20:1.

8. The process according to claim 7, wherein Reactor I has a reaction temperature of from 121 to 170° C., a reaction pressure of from 0.01 to 0.8 MPa, a reaction contacting time of from 2 to 50 seconds, and the molar ratio of NO in nitrogen oxide to oxygen is 4-15:1.

9. The process according to claim 1, wherein Reactor II has a reaction temperature of from 10 to 100° C. and a reaction pressure of from −0.05 to 1.0 MPa, and the molar ratio of $C_1$-$C_4$ alkanol to NO in the effluent I is 1-15:1.

10. The process according to claim 9, wherein Reactor II has a reaction temperature of from 20 to 70° C. and a reaction pressure of from 0.01 to 0.8 MPa, and the molar ratio of $C_1$-$C_4$ alkanol to NO in the effluent I is 1-10:1.

11. The process according to claim 1, wherein the $C_1$-$C_4$ alkanol is selected from the group consisting of methanol, ethanol, n-propanol, and combinations thereof.

12. The process according to claim 1, wherein the rotor in the rotating high-gravity reactor has a rotating speed of from 100 to 5,000 rpm.

13. The process according to claim 12, wherein the rotor in the rotating high-gravity reactor has a rotating speed of from 300 to 3,000 rpm.

14. The process according to claim 1, wherein the molar ratio of NO:$NO_2$ in the effluent I is greater than 1.

15. The process according to claim 4, wherein the porous filler layer comprises an inert filler web, a porous web, a stent or a porous plate.

* * * * *